US008384374B2

(12) United States Patent
Gao

(10) Patent No.: US 8,384,374 B2
(45) Date of Patent: Feb. 26, 2013

(54) APPARATUS FOR AUTOMATICALLY TESTING INTEGRATED CMOS MAGNETORESISTIVE BIOCHIPS

(75) Inventor: Yunhua Gao, Beijing (CN)

(73) Assignee: Dongguan Bosh Biotechnologies, Ltd., Dongguan, Gongdong Province (CN)

( * ) Notice: Subject to any disclaimer, the term of this patent is extended or adjusted under 35 U.S.C. 154(b) by 284 days.

(21) Appl. No.: 12/742,925

(22) PCT Filed: Nov. 12, 2008

(86) PCT No.: PCT/CN2008/073026
§ 371 (c)(1),
(2), (4) Date: Oct. 28, 2010

(87) PCT Pub. No.: WO2009/067924
PCT Pub. Date: Jun. 4, 2009

(65) Prior Publication Data
US 2011/0035176 A1 Feb. 10, 2011

(30) Foreign Application Priority Data
Nov. 14, 2007 (CN) .......................... 2007 1 0177311

(51) Int. Cl.
*G01N 27/74* (2006.01)
*G01R 33/12* (2006.01)

(52) U.S. Cl. ........................................................ 324/204
(58) Field of Classification Search ................... 324/204
See application file for complete search history.

(56) References Cited

U.S. PATENT DOCUMENTS 5,981,297 A 11/1999 Baselt
6,518,747 B2 2/2003 Sager et al.
7,749,445 B2 * 7/2010 Masters ..................... 422/82.01

FOREIGN PATENT DOCUMENTS

| CN | 1475806 A | 2/2004 |
|---|---|---|
| CN | 1510417 A | 7/2004 |
| CN | 1645142 A | 7/2005 |
| CN | 1261755 C | 6/2006 |
| CN | 1815232 A | 8/2006 |
| CN | 101126765 A | 2/2008 |

OTHER PUBLICATIONS

PCT International Search Report for PCT Counterpart Application No. PCT/CN2008/073026 containing Communication relating to the Results of the Partial International Search Report, 6 pgs., (Feb. 19, 2009).

* cited by examiner

*Primary Examiner* — Reena Aurora
(74) *Attorney, Agent, or Firm* — Blakely, Sokoloff, Taylor & Zafman LLP

(57) ABSTRACT

An apparatus for automatically testing CMOS magnetoresistive biochips is disclosed. The apparatus includes: means for directly or indirectly applying physical pressure to the fluid pumping chamber in a cartridge; a liquid injector for injecting liquid into the reaction chamber in the cartridge through an inlet or inlets in fluid connection to said reaction chamber; a CMOS magnetoresistive biochip located in the reaction chamber in the cartridge; means for applying a magnetic field to said CMOS magnetoresistive biochip in the cartridge; an electronic module for communicating with and supplying power as well as control signals to said biochip; a microprocessor to control and coordinate the aforementioned components; and a user interface for information processing. The apparatus provided by the present invention reduces the complexity of operation and enhances the detection sensitivity to a great extent.

18 Claims, 9 Drawing Sheets

APPARATUS FOR AUTOMATICALLY TESTING INTEGRATED CMOS MAGNETORESISTIVE BIOCHIPS

CROSS-REFERENCE TO RELATED APPLICATIONS

This patent application is a U.S. National Phase application under 35 U.S.C. §371 of International Application No. PCT/CN2008/073026, filed on Nov. 12, 2008, entitled AN APPARATUS FOR AUTO-DETECTION OF MAGNETIC SENSITIVE BIOCHIP, which claims priority to Chinese patent application number 200710177311.5, filed Nov. 14, 2007.

FIELD OF THE INVENTION

This invention relates to testing techniques for chemical and biological molecules, cells and microorganism. More particularly, the invention relates to a testing apparatus of biochips using Hall devices, giant magneto-resistive devices or magnetic tunnel junction arrays as magnetic sensors.

BACKGROUND OF THE INVENTION

Magnetoresistive sensors have been widely used in applications such as magnetic hard disks and angular transducers in cars. In 1998, Baselt et al. described using functionalized magnetic particles as tags for detecting biological molecules hybridized to probe biomolecules attached to the surface of giant magneto-resistive (GMR) sensors. More details are described in U.S. Pat. No. 5,981,297, which is hereby incorporated by reference in its entirety. Biochips using magnetoresistive devices as sensors are based on detecting biologically functioned magnetic particles of micrometer or nanometer in diameter. The surface of the biochip is functionalized with antibodies or antigens (probe molecules) that recognize and conjugate specifically with the target molecules in the sample applied onto the surface of the biochip. Paramagnetic particles functionalized with the same type of antibodies or antigens as those on the surface of the biochips are then dropped onto the chip surface. Some of the paramagnetic particles conjugate with the target molecules which have hybridized with the probe molecules on the chip surface, forming a sandwich structure. After free magnetic particles are removed, a magnetic field is applied to the biochip to detect to existence of the paramagnetic particles. Target molecules are quantified by the amount of paramagnetic particles detected.

In Addition to Magnetoresistive (GMR) devices, Magnetic Tunnel Junction (MTJ) devices can also be used as the sensing elements for detecting magnetic particles. Such a biochip is described by Xifu Jiang et al. (Korea) in SIPO China patent application Biosensors and Arrays of Sensor Units (Appl. No. 200310113330), which is hereby incorporated by reference in its entirety. Chao Chen et al. proposed the application of MTJ as the sensing element of biochips in SIPO Pat. No. ZL 0213936. X, which is hereby incorporated by reference in its entirety. In SIPO Pat. Appl. No. 200510005035.5, Lei Wang et al. suggested that $Si_3N_4$ passivation layer could be replaced by plastic passivation layer.

Researches in the past decade has shown that, as a new technology platform in the development of various bio-sensor chips, magnetoresistive biosensor is a very good candidate for high speed, high sensitivity and high throughput detection of biomolecules at a reasonable cost. At the 2006 Biosensor Congress in Toronto, researchers with Philips reported that there had been more than 30 groups worldwide developing magnetoresistive biosensors.

In order to improve test throughput and the functionality of magnetoresistive biosensor chips, one can enlarge the array size of the magnetoresistive sensors, spot many different kinds of probing molecules on the array, and detect numerous target molecules simultaneously. A practical issue related to such a design is that the number of conductor lines connecting the sensing element and the area occupied by the conductor lines increase proportionally with the array size. The area taken by conductor lines and the complexity related to laying out these lines make large scale integration of magnetoresistive sensor array practically impossible. Additionally, the large number of bonding wires necessary for connecting the conductor lines on the chip to a testing apparatus cause tremendous amount of difficulty for packaging and testing. To overcome these issues, one can integrate the magnetoresistive sensor array with a large scale integrated CMOS circuit. The three dimensional architecture of magnetoresistive sensor array on top of the CMOS circuit makes a biochip with a large array of magnetoresistive sensors feasible. Consequently, detecting a large number of target molecules using a biochip with a large array of magnetoresistive sensors becomes a reality.

Even though there are numerous publications on biochips using magnetoresistive sensors, what is still needed is a testing apparatus for biosensors and biochips using magnetoresistive or magnetic tunnel junction devices as the sensing element, particularly a testing apparatus for integrated CMOS magnetoresistive biochips.

SUMMARY OF THE INVENTION

Addressing the shortcomings in the prior art, the present invention provides a testing system for integrated CMOS magnetoresistive biochips. The apparatus of the present invention offers high sensitivity and high speed with automated testing procedure.

The integrated CMOS magnetoresistive biochips referred here are defined as chips of CMOS circuit integrated with arrays of magnetic sensors, including but not limited to giant magnetoresistive (GMR) sensors, magnetic tunnel unction sensors, or Hall effect sensors. The main structures of the biochips are the CMOS integrated circuit manufactured on the monocrystalline silicon substrate, magnetic tunnel and magnetoresistance structure being on the integrated circuit, passivation layer for protection being on the magnetic tunnel and magnetoresistance structure, and biochemical surface being on the passivation layer for protection.

The present invention provides automatic testing apparatus for integrated CMOS magnetoresistive biochips comprising means for directly or indirectly applying pressure to a reagent reservoir or a plurality of reservoirs in a cartridge with at least one reaction chamber where the integrated CMOS magnetoresistive biochip is located. Under said pressure, the reagent in the reservoir or reservoirs flows into the reaction chamber via a micro-channel or a plurality of micro-channels. The apparatus further comprises a fluid injection system connected to the cartridge, injecting liquid into the reaction chamber via microfluidic channels. The apparatus further comprises means for applying a magnetic field, either positive or negative, with a required magnitude to the integrated CMOS magnetoresistive biochips in said cartridge. The apparatus further comprises an electronic module to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal. The apparatus further comprises a microprocessor to control and coordinate the aforementioned components: said means for directly or indirectly applying pressure to the reagent reservoir in said cartridge, said liquid injection system connected to said cartridge used to inject liquid into said microfluidic channel or channels connected to said reaction chamber in said cartridge, said means for applying positive or negative magnetic field to said integrated CMOS magnetoresistive biochip, said electronic module for supplying power and controlling signal to said integrated CMOS magnetoresistive biochip in said cartridge, testing the information stored in the sensing elements of said integrated CMOS magnetoresistive biochip, and converting the tested analog signal to digital signal; and to process information measured under different magnetic fields. The apparatus further comprises a user interface to receive and display information from said microprocessor.

In one embodiment, the means in the above apparatus for applying pressure to the reagent reservoir comprises an electrical motor or electrical stepping motor. The linear actuator of said motor puts pressure on the wall of the reagent reservoir, pushing the reagent to flow into the reaction chamber via a micro-channel in fluid connection to the reservoir at one end and to the reaction chamber at the other end. The reagent flows out of the exit of the reaction chamber into a waste reservoir which has a pressure release hole to facilitate the fluid flow.

In another embodiment, the means for applying pressure to the reagent reservoir comprises means to increase air pressure in the reagent reservoir. The air pressure causes the reagent to flow into the reaction chamber via a micro-channel in fluid connection to the reservoir. The reagent flows out of the exit of the reaction chamber into a waste reservoir which has a pressure release hole to facilitate the fluid flow.

In yet another embodiment, the means for applying pressure to the reagent reservoir comprises means to create a vacuum at the exit end of the reaction chamber connected to the waste reservoir in the cartridge. The vacuum created at the exit of the reaction chamber causes the reagent to flow into the reaction chamber via a micro-channel in fluid connection to the reagent reservoir. The reagent flows out of the exit of the reaction chamber into a waste reservoir.

In the automatic testing apparatus described above, one embodiment of the fluid injection system comprises a plurality of syringes delivering fluid into the reaction chamber via inlets in fluid connection with the reaction chamber through microfluidic channels. Controlled and coordinated by a microprocessor, electrical stepping motors powered by their drive circuits actuate the syringes. The injection needles of the syringes are driven by a stepping motor controlled by the microprocessor to achieve fluid-tight coupling with the inlets. The liquid injected by said syringes may contain sample, magnetic particles or buffer solutions.

In the automatic testing apparatus described above, the direction of the magnetic field from the means for applying magnetic fields can be adjusted manually or automatically is according to the instructions of said microprocessor.

In the automatic testing apparatus described above, said integrated CMOS magnetoresistive biochip is an electromagnetic device comprising the large scale integrated CMOS circuit integrated with magnetoresistive device manufactured with semiconductor processing technology, including CMOS circuit and magnetic tunnel junction arrays, or CMOS circuit and giant magneto-resistive devices, or CMOS circuit and Hall magneto-resistance devices.

The present invention provides another automatic testing apparatus for integrated CMOS magnetoresistive biochips comprising means for directly or indirectly applying pressure to a reagent reservoir or a plurality of reservoirs in a cartridge with at least one reaction chamber where the integrated CMOS magnetoresistive biochip is located. Under said pressure, the reagent in the reservoir or reservoirs flows into the reaction chamber via a micro-channel or a plurality of micro-channels. The apparatus further comprises means for applying a magnetic field, either positive or negative, with a required magnitude to the integrated CMOS magnetoresistive biochips in said cartridge. The apparatus further comprises an electronic module to supply power and control signal to said integrated CMOS magnetoresistive biochip in said cartridge, test the information stored in the sensing elements of the integrated CMOS magnetoresistive biochip, and convert the tested analog signal to digital signal. The apparatus further comprises a microprocessor to control and coordinate the aforementioned components: said means for directly or indirectly applying pressure to the reagent reservoir in said cartridge, said means for applying positive or negative magnetic field to said integrated CMOS magnetoresistive biochip, said electronic module for supplying power and controlling signal to said integrated CMOS magnetoresistive biochip in said cartridge, communicating with a large scale integrated CMOS circuit on the biochip, testing the information stored in the sensing elements of said integrated CMOS magnetoresistive biochip, and converting the tested analog signal to digital signal; and to process information measured under different magnetic fields. The apparatus further comprises a user interface to receive and display information from said microprocessor.

In one embodiment, the means in the above apparatus for applying pressure to a reagent reservoir comprises an electrical motor or electrical stepping motor. The linear actuator of said motor puts pressure on the wall of the reagent reservoir, pushing the reagent to flow into the reaction chamber via a micro-channel in fluid connection to the reservoir at one end and to the reaction chamber at the other end. The reagent flows out of the exit of the reaction chamber into a waste reservoir which has a pressure release hole to facilitate the fluid flow.

In another embodiment, the means for applying pressure to a reagent reservoir comprises means to increase air pressure in the reagent reservoir. The air pressure causes the reagent to flow into the reaction chamber via a micro-channel. The reagent flows out of the exit of the reaction chamber into a waste reservoir which has a pressure release hole to facilitate the fluid flow.

In yet another embodiment, the means for applying pressure to a reagent reservoir comprises means to create a vacuum at exit end of the reaction chamber connected to the waste reservoir in the cartridge. The vacuum created at the exit of the reaction chamber causes the reagent to flow into the reaction chamber via a micro-channel in fluid connection to the reagent reservoir. The reagent flows out of the exit of the reaction chamber into a waste reservoir.

In the automatic testing apparatus described above, the direction of the magnetic field from the means for applying magnetic fields can be adjusted manually or automatically is according to the instructions of said microprocessor. The integrated CMOS magnetoresistive biochip is an electromagnetic device comprising the large scale integrated CMOS circuit integrated with magnetoresistive device manufactured with semiconductor processing technology, including CMOS circuit and magnetic tunnel junction arrays, or CMOS circuit and giant magneto-resistive devices, or CMOS circuit and Hall magneto-resistance devices.

The present invention provides yet another automatic testing apparatus for integrated CMOS magnetoresistive biochips, comprising a fluid injection system connected to the cartridge, injecting liquid into the reaction chamber via microfluidic channels. In one embodiment, the fluid injection system comprises a plurality of syringes delivering fluid into the reaction chamber via inlets in fluid connection with the reaction chamber through microfluidic channels. Controlled and coordinated by a microprocessor, electrical stepping motors powered by their drive circuits actuate the syringes. The injection needles of the syringes are driven by a stepping motor controlled by the microprocessor to achieve fluid-tight coupling with the inlets. The liquid injected by said syringes may contain sample, magnetic particles or buffer solutions. The apparatus further comprises means for applying a magnetic field, either positive or negative, with a required magnitude to the integrated CMOS magnetoresistive biochips in said cartridge. The apparatus further comprises an electronic module to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal. The apparatus further comprises a microprocessor to control and coordinate the aforementioned components: said liquid injection system connected to said cartridge used to inject liquid into said microfluidic channel or channels connected to said reaction chamber in said cartridge, said means for applying positive or negative magnetic field to said integrated CMOS magnetoresistive biochip, said electronic module for supplying power and controlling signal to said integrated CMOS magnetoresistive biochip in said cartridge, testing the information stored in the sensing elements of said integrated CMOS magnetoresistive biochip, and converting the tested analog signal to digital signal; and to process information measured under different magnetic fields. The apparatus further comprises a user interface to receive and display information from said microprocessor.

The present invention provides yet another automatic testing apparatus for integrated CMOS magnetoresistive biochips, comprising means for applying a magnetic field, either positive or negative, with a required magnitude to the integrated CMOS magnetoresistive biochips in said cartridge. The apparatus further comprises an electronic module to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal. The apparatus further comprises a microprocessor to control and coordinate the aforementioned components: said means for applying positive or negative magnetic field to said integrated CMOS magnetoresistive biochip, said electronic module for supplying power and controlling signal to said integrated CMOS magnetoresistive biochip in said cartridge, testing the information stored in the sensing elements of said integrated CMOS magnetoresistive biochip, and converting the tested analog signal to digital signal; and to process information measured under different magnetic fields. The apparatus further comprises a user interface to receive and display information from said microprocessor.

ADVANTAGES OF THE INVENTION

The present invention provides automatic testing apparatus for biochips using magnetoresistive sensors. Said apparatus reduce the complexity of operation and the consumption of reagents and offers high detection speed with good repeatability by using automatic liquid injectors with the microfluidic cartridge. The combination of integrated CMOS magnetoresistive biochips and microfluidic systems enhances the detection sensitivity to a great extent. The actuation of the reagent reservoir on the cartridge by the means for applying pressure in said testing apparatus forms a highly efficient microfluidic pump and reduces the cost of the cartridge effectively.

BRIEF DESCRIPTION OF THE DRAWINGS

FIG. 1a is the front view of the cartridge of magnetoresistive sensor biochips in the first embodiment.

FIG. 1b is the left view of FIG. 1a.

FIG. 3b is the left view of FIG. 3a.

FIG. 5b is the left view of FIG. 5a.

REFERENCE OF THE NUMERICAL LABELS IN THE DRAWINGS AND DESCRIPTION

Figures 1A, 1B:
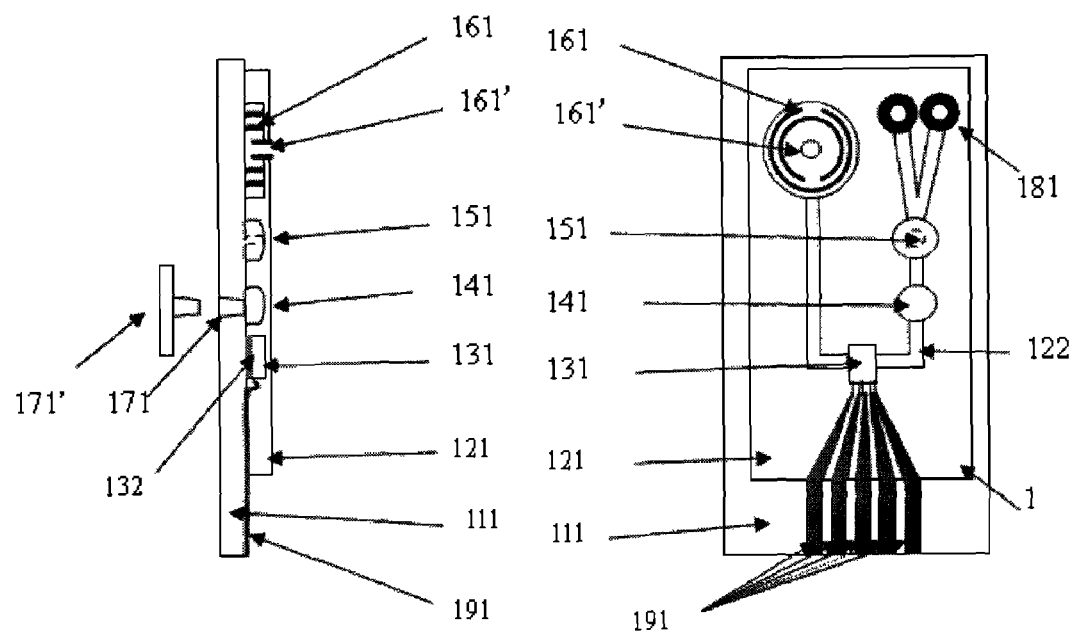

1 A cartridge, which comprises either all or some of the following features:

| 111 | The substrate, | | |
|---|---|---|---|
| 121 | The cartridge layer with microchannels, | 122 | Microfluidic channels |
| 131 | The reaction chamber, | 132 | The biochip |
| 141 | The reagent reservoir, | 142 | The liquid reservoir |
| 151 | The pump chamber, | 152 | The pressure chamber, |
| 153 | Inlets and outlets of liquid or air | | |
| 161 | The waste reservoir, | 161' | Waste outlets |
| 171 | The opening of the reagent reservoir, | | |
| 171' | The sealing cap of the reagent reservoir | | |
| 181 | Fluid inlets | | |
| 191 | Electrical conductive lines | | |

2 Means for applying pressure, which comprises either all or some of the following features:
21 Control circuits of the stepping motor,
22 The stepping motor,
23 The driving rod,
24 Coupling pipes, 25 The apparatus for generating and regulating pressured liquid or air
3 A liquid injection system comprises:
311, 312 Injectors
321, 322, 323 The electrical stepping motor
33 Control circuit of the stepping motor,
34 Injection needle
4 Means for generating a magnetic field comprises
41 Electromagnets,
42 The power circuit for the electromagnets,
43 A device for adjusting the direction of the magnetic field
5 Electronic module for controlling and reading information from said biochip
6 A microprocessor
7 A user interface

DETAILED DESCRIPTION OF THE PREFERRED EMBODIMENT

The cartridge described in the present invention serves as a carrier for magnetoresistive sensor biochips to facilitate their connection and interaction with the testing apparatus in the present invention. The microfluidic channels in said cartridge make the biochemical reaction easier on biochips, enhancing its detection sensitivity. The concrete structure and function of said cartridge have been described in detail in SIPO China patent application No. 200710175624.7 on Oct. 9, 2007, which is hereby incorporated by reference in its entirety.

Embodiment 1

Cartridge of Magnetoresistive Sensor Biochips

Refer to FIGS. 1a and 1b. Substrate 111 of cartridge 1 can be made of glass, ceramics, single crystal silicon with an layer of silicon dioxide on the surface, or polymer. Orifice 171 of reagent reservoir 141 on substrate 111 serves as inlet of reagents. Orifice 171 can be sealed fluid-tight by cap 171'. In contact with substrate 111 is the channel and chamber layer 121 of the cartridge, wherein a plurality of channels and chambers are formed. There are at least one reaction chamber 131, one reagent reservoir 141, one pump chamber 151, one waste reservoir 161 and more than one fluid inlet 181 in connection with microfluidic channels 122. Inlets 181 are for the injection of reaction reagent, buffer solution or rinsing buffer into reaction chamber 131. Pump chamber 151 is capped with a layer of flexible material which can bend under pressure, hence pumping the reagent in reservoir 141 into reaction chamber 131. Changing the direction of the applied pressure changes the direction of fluid flow in reaction chamber 131. Such an oscillation movement of reagent improves the efficiency of the biochemical reaction of molecules in the reagent with the molecules on the surface of biochip 132 located in reaction chamber 131. Waste reservoir 161 consists of a plurality of concentric circular micro-channels and orifice 161' as the waste outlet. When reagent is moved back and forth through reaction chamber 131, the structure of waste reservoir 161 reduces the chance of cross contamination of the reagent in reaction with the waste already in waste reservoir 161. Biochip 132, using Hall effect, giant magnetoresistive or magnetic tunnel junction devices as sensors, is placed in reaction chamber 131, wherein the CMOS circuit on biochip 132 is connected with the testing apparatus outside cartridge 1 through a plurality of conducting lines 191 on the cartridge 1.

Embodiment 2

Figure 2:
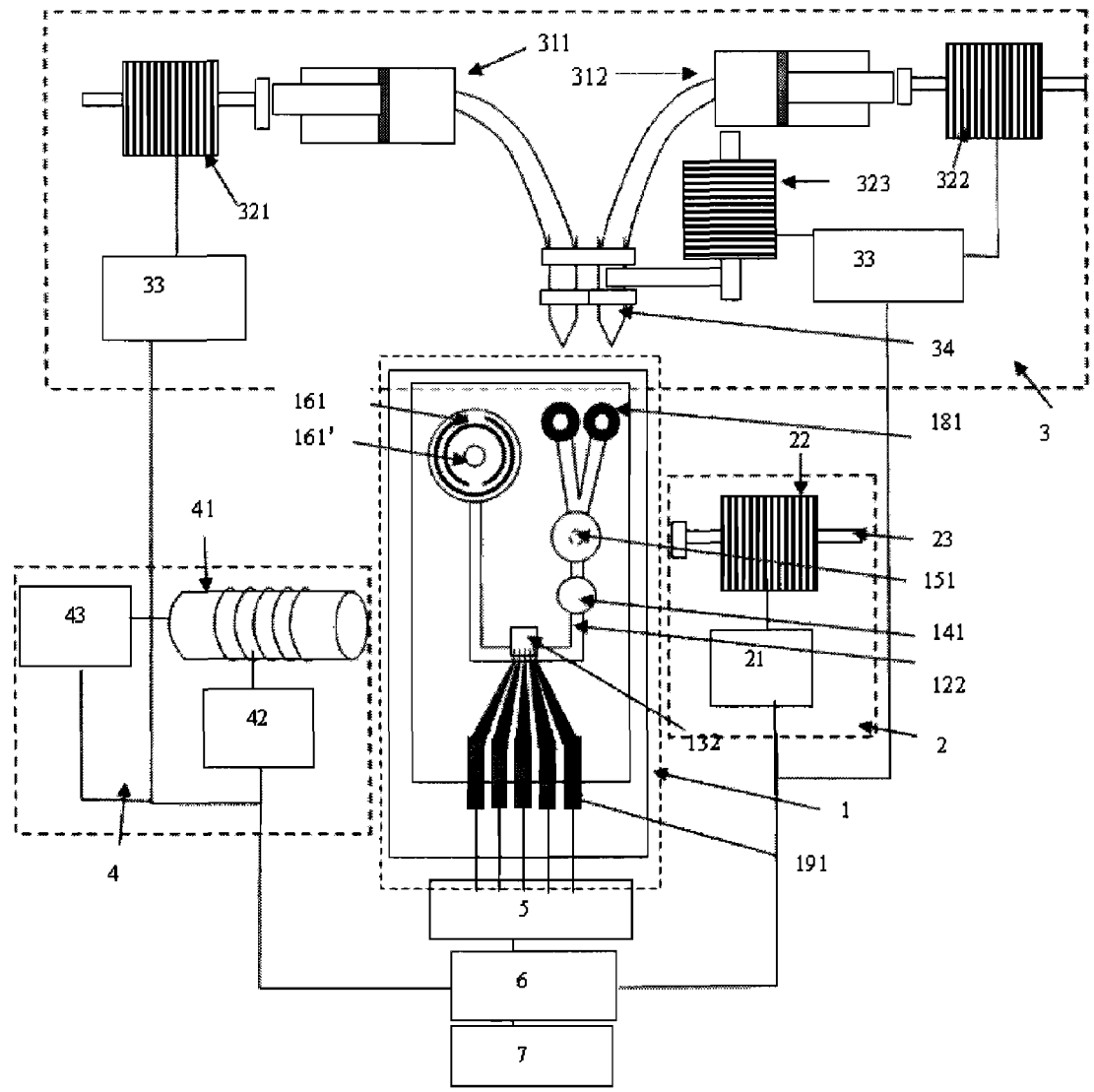
FIG. 2 is a block diagram of the testing apparatus for magnetoresistive sensor biochips in the second embodiment.

The testing apparatus for magnetoresistive sensor biochips shown in FIG. 2 includes: 2, means for applying pressure, which comprises a control circuitry 21 for electrical motor or electrical stepping motor 22 and driving rod 23, wherein the output signal of circuit 21 is controlled by microprocessor 6. By applying pressure either to pump chamber 151, which is in fluid connection with reagent reservoir 141 in cartridge 1, or directly to reagent reservoir 141, driving rod 23 pushes fluid into reaction chamber 131 in said cartridge 1.

Besides an electrical motor or electrical stepping motor, other linear actuating devices such as piezoelectric devices can serve as 2, the means for applying pressure to either pump chamber 151 or reagent reservoir 141.

The testing apparatus shown in FIG. 2 further includes fluid injection system 3, which comprises the first injector 311 and the second injector 312; the first stepping electrical motor 321, the second stepping electrical motor 322, the third stepping electrical motor 323; the control circuits for the stepping motors 33; and injection needle 34. The driving rod of the first electrical stepping motor 321 actuates the first injector 311; the driving rod of the second electrical stepping motor 322 actuates the second injector 312. Injection needles 34, which are connected with liquid injectors 311 and 312, are driven by the third electrical stepping motor 323 to form fluid-tight connection with fluid inlets 181 in cartridge 1. The output of control circuits 33 is regulated by microprocessor 6. Driven by electrical stepping motors 321 and 322, the first injector 311 and second injector 312 inject fluid, either successively or simultaneously, into reaction chamber 131 via an inlet or inlets 181 connected to reaction chamber 131 through microfluidic channels 122. Said liquid stream can also drive the fluid in microfluidic channels 122 into the waste reservoir 161 through the reaction chamber 131 in said cartridge 1 to drain the waste through liquid outlet 161'. The liquid stream ejected by fluid injection system 3 contains biomolecules, magnetic particles or buffer solution.

The testing apparatus shown in FIG. 2 further includes 4, the means for generating a magnetic field, which comprises electromagnet 41 in series connection with power circuit 42. The operation of power circuit 42 is controlled by microprocessor 6. Power circuit 42 provides either a positive or negative current with particular amplitude to the electromagnet. Accordingly, the electromagnet applies either a positive or negative magnetic field on to the integrated CMOS magnetoresistive biochip 132 under test.

There can be two directions for the magnetic field applied by electromagnet 41, either parallel or perpendicular to the surface of integrated CMOS magnetoresistive biochip 132. With proper signal processing scheme, field in either direction can magnetize the magnetic particles to stimulate magnetoresistive sensor biochip and test the existence of magnetic particles. In the present invention, the field direction is perpendicular to the surface of the integrated CMOS magnetoresistive biochip. Device 43 is used to tune the direction of electromagnet 41 to ensure that the magnetic field is perpendicular to magnetoresistive sensor biochip 132. According to the response of magnetoresistive sensor biochips 132 to the magnetic field applied by electromagnet 41, microprocessor 6 can calculate the direction of magnetic field, and then instructs device 43 to adjust electromagnet 41 accordingly.

Electronic module 5, which is used for controlling and reading information from the biochip 132, is connected with biochip 132 via conductive lines 191 on substrate 111 on cartridge 1. The function of electronic module 5 is to supply power and control signals for magnetoresistive sensor biochip 132 in said cartridge 1, test the information stored in each magnetoresistive sensor elements in biochip 132, and perform analog-to-digital conversion of the results;

Microprocessor 6 controls and coordinates the operation of the means for applying pressure 2, fluid injection system 3, means for applying magnetic field 4 and electronic module 5. Additionally, microprocessor 6 is also used to processes information and test results, such as performing the necessary calculation to remove background noise and extract out the user data.

User interface 7 is connected to microprocessor 6 to receive users' instruction and display the test condition and results.

Procedures of said apparatus are shown below:
Step 1: Turn ON the power supply of the test apparatus;
Step 2: Inject samples and functionalized magnetic particles into reagent reservoir 141, and put the cartridge into the testing apparatus in the present invention;
Step 3: Input testing conditions and requirements through user interface 7;
Step 4: Under the instruction of microprocessor 6, the means for applying pressure 2 applies pressure to pump chamber 151 to inject the mixed liquid stream in reagent reservoir 141 into reaction chamber 131 via micro-channel 122, wherein the bio molecules in the liquid hybridize with biological probes on biochip 132;
Step 5: Controlled by microprocessor 6, fluid injection system 3 injects rinsing buffer into reaction chamber 131 to remove the molecules and magnetic particles which are non-specifically bound on the surface of biochip 132.
Step 6: Controlled by microprocessor 6, power circuit 42 for electromagnet 41 applies a magnetic field to magnetoresistive sensor biochip 132.
Step 7: Controlled by microprocessor 6, electronic module 5 read the information of magnetoresistive sensor devices.
Step 8: Microprocessor 6 processes the tested results under different magnetic fields to get the results.
Step 9: User interface 7 displays the results.

Embodiment 3

Fabrication and Materials of the Cartridge for Magnetoresistive Sensor Biochips

Figure 3A:
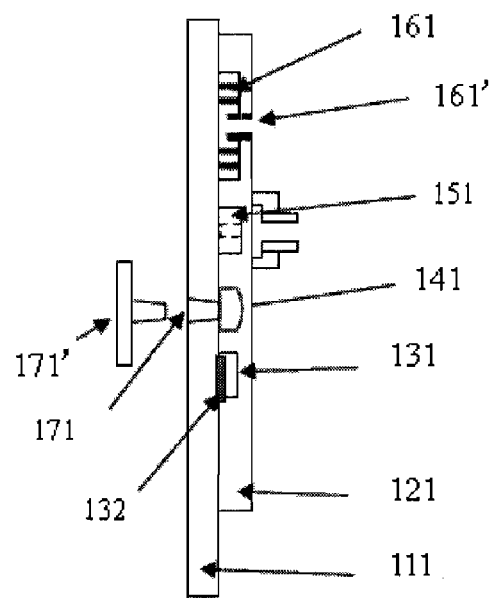
FIG. 3a is a front view of the cartridge of magnetoresistive sensor biochips in the third embodiment.
Figure 3B:
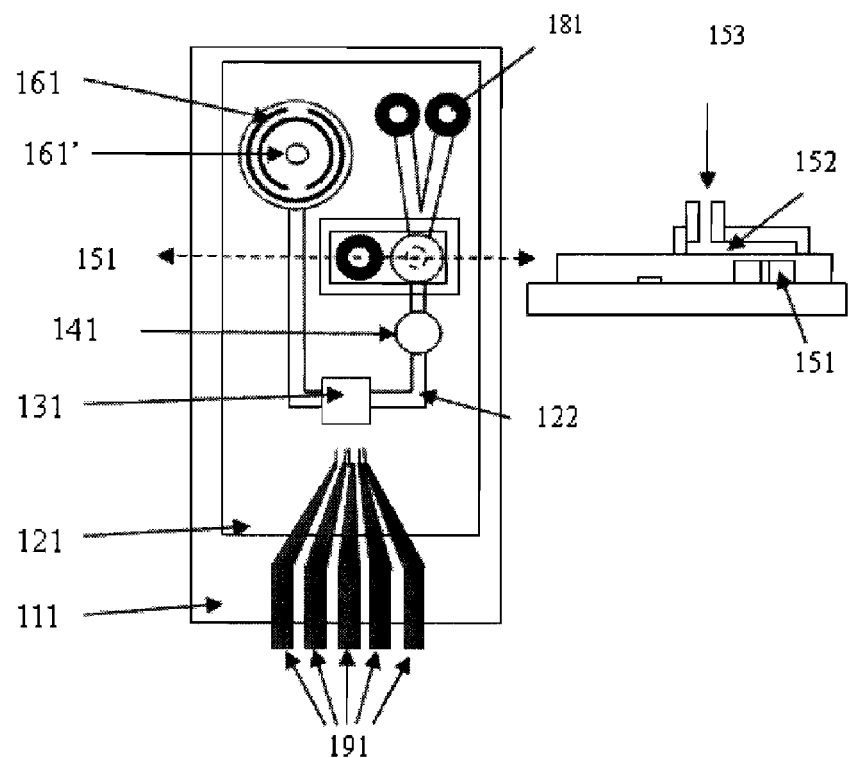

FIGS. 3a and 3b show said cartridge, wherein substrate 111 can be made of glass, ceramics, single crystal silicon with an layer of silicon dioxide on the surface or polymer. Orifice 171 of reagent reservoir 141 on substrate 111 serves as inlet of reagents. Orifice 171 can be sealed fluid-tight by cap 171'. In contact with substrate 111 is the channel and chamber layer 121 of the cartridge, wherein a plurality of channels and chambers are formed. Channel and chamber layer 121 can be made of flexible material such as silastic by molding, or plastic materials such as polymethylmethacrylate (PMMA), polycarbonate (PC), polypropylene (PP), nylon, polytetrafluoroethene, and polyether-ether-ketone. Microfluidic channels 122 and reagent reservoir 141 are fabricated by molding, while flexible material such as PDMS should be used as the cap of pump chamber 151. There are at least one reaction chamber 131, one reagent reservoir 141, one pump chamber 151, one waste reservoir 161 and more than one fluid inlet 181 in connection with microfluidic channels 122. Inlets 181 are for the injection of reaction reagent, buffer solution or rinsing buffer into reaction chamber 131. Pressure chamber 152 lies above pump chamber 151. Orifice 153 is used to connect pressure chamber 152 with an equipment which can create either a negative or positive pressure in chamber 152 with liquid or gas. Pump chamber 151 is capped with a layer of flexible material which can bend under pressure, pumping the reagent in reservoir 141 into reaction chamber 131. Changing the direction of the applied pressure in chamber 152 changes the direction of fluid flow in reaction chamber 131. Such an oscillation movement of reagent improves the efficiency of the biochemical reaction of molecules in the reagent with the molecules on the surface of biochip 132 located in reaction chamber 131. Waste reservoir 161 consists of a plurality of concentric circular micro-channels and orifice 161' as the waste outlet. When reagent is moved back and forth through reaction chamber 131, the structure of waste reservoir 161 reduces the chance of cross contamination of the reagent in reaction with the waste already in waste reservoir 161. Biochip 132, using Hall effect, giant magnetoresistive or magnetic tunnel junction devices as sensors, is placed in reaction chamber 131, wherein the CMOS circuit on biochip 132 is connected with the testing apparatus outside cartridge 1 through a plurality of conducting lines 191 on the cartridge 1. Layer 121 can be made of flexible material such as polydimethylsiloxane (PDMS) or rubber, or the same material as that of 111, but flexible material should be used as the capping layer of pump chamber 151.

Embodiment 4

Figure 4:
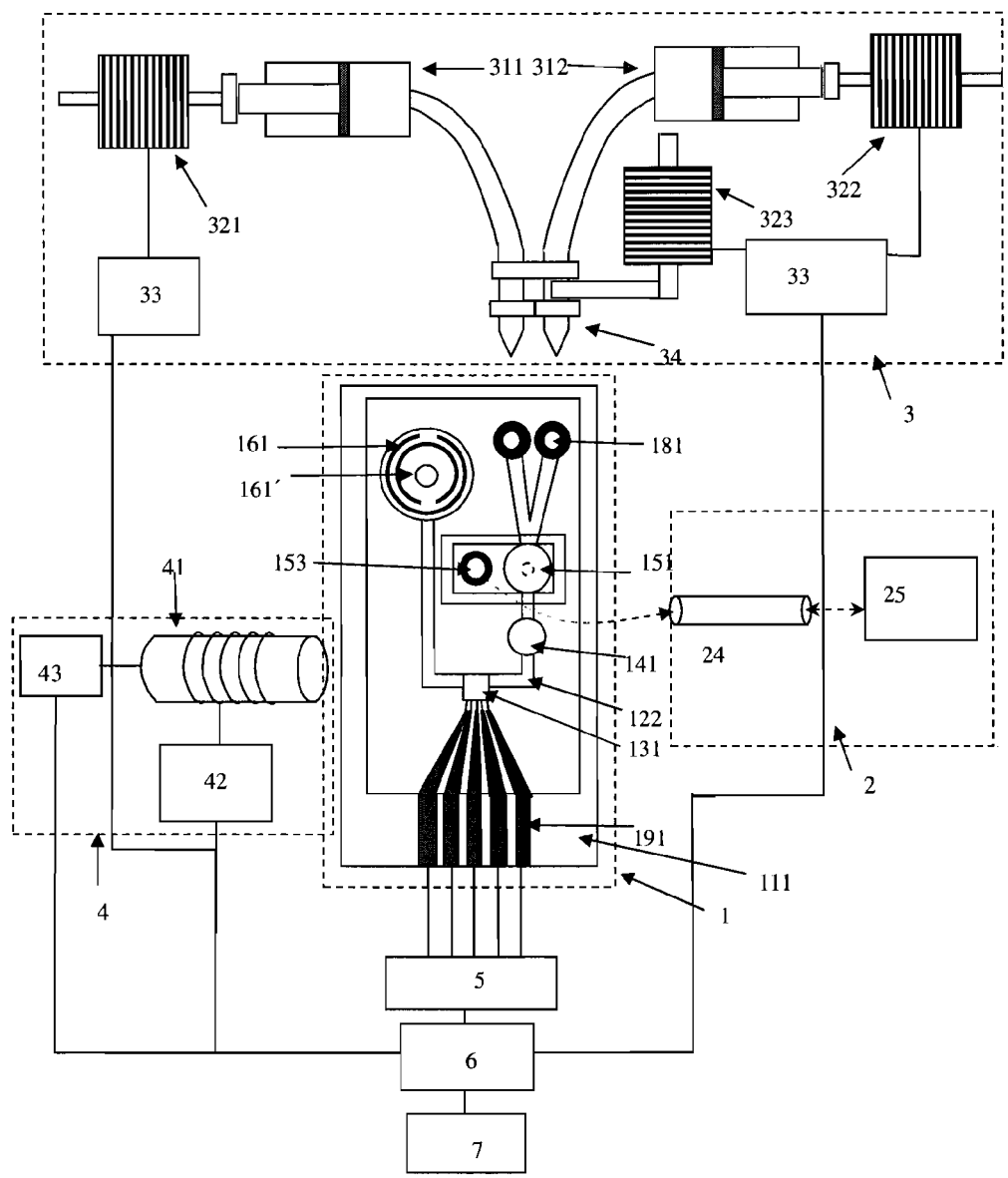
FIG. 4 shows the testing apparatus for magnetoresistive sensor biochips in the fourth embodiment.

The test apparatus for magnetoresistive sensor biochips in FIG. 4 includes means for applying pressure 2, which comprises the means for creating a vacuum and/or pressure 25 and coupling pipe 24. Coupling pipe 24 connects with the means for creating a vacuum and/or pressure 25 at one end, and orifice 153 of pressure chamber 152 at the other end. Since pump chamber 151 is capped by a layer of flexible material, the increase or decrease of pressure in pressure chamber 152 by the means for creating a vacuum and/or pressure 25 will drive pump chamber 151 to contract or expand and push the liquid in reagent reservoir 141 through reaction chamber 131.

The testing apparatus shown in FIG. 4 further includes fluid injection system 3 which comprises: the first injector 311 and the second injector 312; the first stepping electrical motor 321, the second stepping electrical motor 322, the third stepping electrical motor 323; the control circuits for the first and second stepping motors 33; injection needle 34. The driving rod of the first electrical stepping motor 321 actuates the first injector 311; the driving rod of the second electrical stepping motor 322 actuates the second injector 312. Injection needles 34, which are connected with liquid injectors 311 and 312, are driven by the third electrical stepping motor 323 to form fluid-tight connection with fluid inlet 181 in cartridge 1. The output of control circuits 33 is regulated by microprocessor 6. Driven by electrical stepping motors 321 and 322, the first injector 311 and second injector 312 inject fluid, either successively or simultaneously, into reaction chamber 131 via an inlet or inlets 181 connected to reaction chamber 131 through microfluidic channels 122. Said liquid stream can also drive the fluid in microfluidic channels 122 into the waste reservoir 161 through the reaction chamber 131 in said cartridge 1 to drain the waste through liquid outlet 161'. The liquid stream ejected by fluid injection system 3 contains biomolecules, magnetic particles or buffer solution.

The testing apparatus shown in FIG. 4 further includes 4, the means for generating a magnetic field, which comprises electromagnet 41 in series connection with power circuit 42. The operation of power circuit 42 is controlled by microprocessor 6. Power circuit 42 provides either a positive or negative current with a particular amplitude to the electromagnet. Accordingly, the electromagnet applies either a positive or negative magnetic field on to the integrated CMOS magnetoresistive biochips 132 under test.

There can be two directions for the magnetic field applied by electromagnet 41, either parallel or perpendicular to the surface of integrated CMOS magnetoresistive biochip 132. With proper signal processing scheme, field in either direction can magnetize the magnetic particles to stimulate magnetoresistive sensor biochip and test the existence of magnetic particles. In the present invention, the field direction is perpendicular to the surface of the integrated CMOS magnetoresistive biochip. Device 43 is used to tune the direction of electromagnet 41 to ensure that the magnetic field is perpendicular to magnetoresistive sensor biochip 132.

According to the response of magnetoresistive sensor biochips 132 to the magnetic field applied by electromagnet 41, microprocessor 6 can calculate the direction of magnetic field, and then instructs device 43 to adjust electromagnet 41 accordingly.

Electronic module 5, which is used for controlling and reading information from the biochip 132, is connected with biochip 132 via conductive lines 191 on substrate 111 on cartridge 1. The function of electronic module 5 is supply power and control signals for magnetoresistive sensor biochips 132 in said cartridge 1, test the information stored in each magnetoresistive sensor elements in biochip 132, and perform analog-to-digital conversion of the results;

Microprocessor 6 controls and coordinates the operation of the means for applying pressure 2, fluid injection system 3, means for generating a magnetic field 4 and electronic module 5. Additionally, microprocessor 6 is also used to processes information and test results, such as performing the necessary calculation to remove background noise and extract out the user data.

User interface 7 is connected to said microprocessor 6 to receive users' instruction and display the test condition and results.

Embodiment 5

Fabrication of Cartridge 1 for Magnetoresistive Sensor Biochips

Figure 5A:
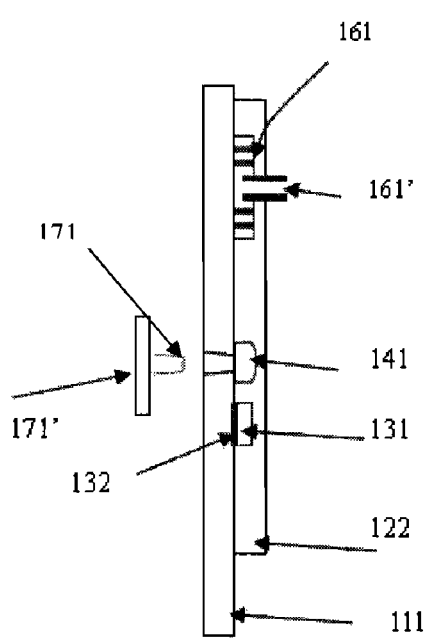
FIG. 5a shows a front view of the cartridge of magnetoresistive sensor biochips in the fifth embodiment.
Figure 5B:
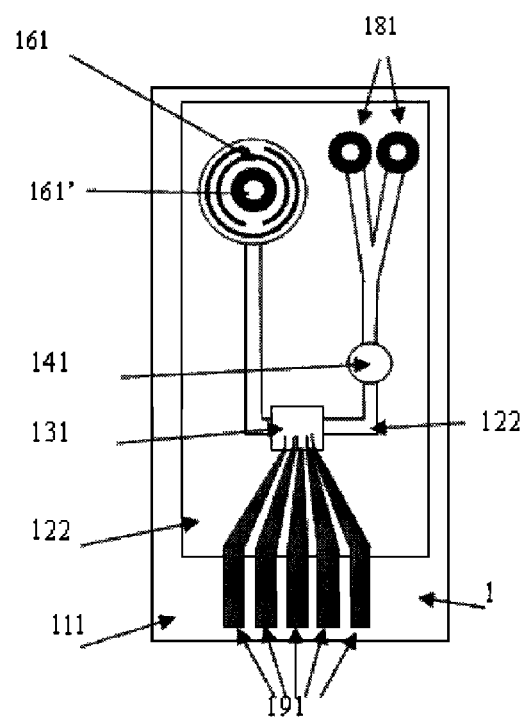

FIGS. 5a and 5b show said cartridge 1, wherein the substrate 111 can be made of glass, ceramics, single crystal silicon with a layer of silicon dioxide on the surface or polymer. Orifice 171 of reagent reservoir 141 on substrate 111 serves as inlet of reagents. Orifice 171 can be sealed fluid-tight by cap 171. In contact with substrate 111 is the channel and chamber layer 121 of the cartridge, wherein a plurality of channels and chambers are formed. The material for layer 121 can be glass, ceramics or single crystal silicon with a layer of silicon dioxide on the surface, and the channels and chambers can be made by traditional wet etching or dry etching technologies. Layer 121 can also be made of plastic materials such as polymethylmethacrylate (PMMA), polycarbonate (PC), polypropylene (PP), nylon, polytetrafluoroethene, polyether-ether-ketone and silastic, and the channels and chambers can be formed by molding. The material of substrate 111 can be the same as or different from that of channel and chamber layer 121. In layer 121 there are at least one reaction chamber 131, one reagent reservoir 141, one waste reservoir 161 and more than one liquid inlet 181. Inlets 181 is used for injecting reagent, probe molecules, buffer solution or rinsing buffer into reaction chamber 131 via micro-channel 122. Said liquid inlets 181 may be open before use, but sealed fluid-tight with injection needle 34 when it is used to inject liquid. Waste reservoir 161 consists of a plurality of concentric circular micro-channels and orifice 161' as the waste outlet. When reagent is moved back and forth through reaction chamber 131, the structure of waste reservoir 161 reduces the chance of cross contamination of the reagent in reaction with the waste already in waste reservoir 161. Biochip 132 using Hall, giant magnetoresistive or magnetic tunnel junction sensor array are placed in the reaction chamber 131 and connected with the testing apparatus via a plurality of connective lines 191 on cartridge 1.

Embodiment 6

Figure 6:
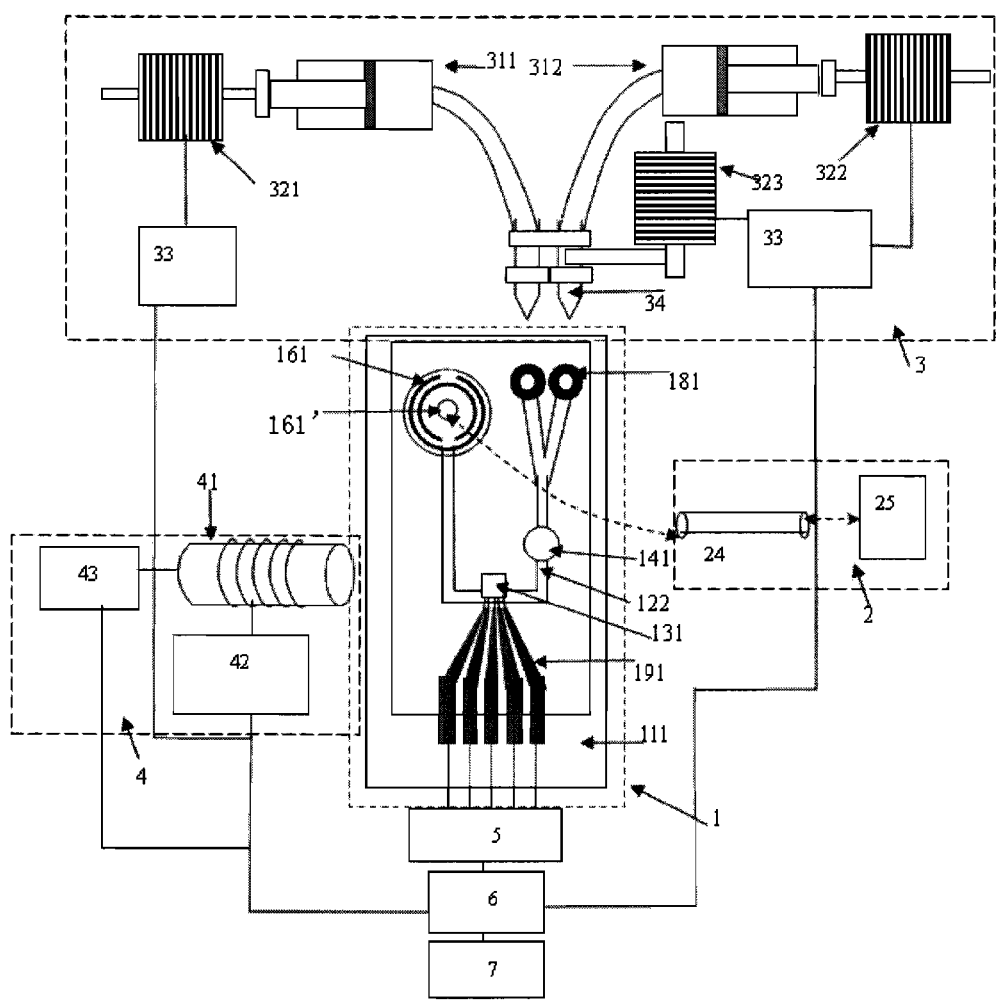
FIG. 6 shows the testing apparatus for magnetoresistive sensor biochips in the sixth embodiment.

Shown in FIG. 6, the testing apparatus for magnetoresistive sensor biochips comprises means for applying pressure 2, comprising the means for creating a vacuum and/or pressure 25 and coupling pipe 24. Coupling pipe 24 is connected to the means for creating a vacuum and/or pressure 25 at one end, and orifice 161' on waste reservoir 161 in cartridge 1 at the other end. The increase or decrease in pressure by the means for creating a vacuum and/or pressure 25 will move the fluid in microfluidic channels 122 through reaction chamber 131.

The testing apparatus for magnetoresistive sensor biochips shown in FIG. 6 further comprises fluid injection system 3 which consists of the first injector 311 and the second injector 312; the first stepping electrical motor 321, the second stepping electrical motor 322, the third stepping electrical motor 323; the control circuit for the electrical stepping motors 33; and injection needles 34. The driving rod of the first electrical stepping motor 321 actuates the first injector 311; the driving rod of the second electrical stepping motor 322 actuates the second injector 312. Injection needles 34, which are connected with liquid injectors 311 and 312, are driven by the third electrical stepping motor 323 to form fluid-tight connection with fluid inlet 181 in cartridge 1. The output of control circuits 33 is regulated by microprocessor 6. Driven by electrical stepping motors 321 and 322, the first injector 311 and second injector 312 inject fluid, either successively or simultaneously, into reaction chamber 131 via an inlet or inlets 181 connected to reaction chamber 131 through microfluidic channels 122. Said liquid stream can also drive the fluid in microfluidic channels 122 into the waste reservoir 161 through the reaction chamber 131 in said cartridge 1 to drain the waste through liquid outlet 161'. The liquid stream ejected by fluid injection system 3 contains biomolecules, magnetic particles or buffer solution.

The testing apparatus shown in FIG. 6 further includes 4, the means for generating a magnetic field, which comprises electromagnet 41 in series connection with power circuit 42. The operation of power circuit 42 is controlled by microprocessor 6. Power circuit 42 provides either a positive or negative current with a particular amplitude to the electromagnet. Accordingly, the electromagnet applies either a positive or negative magnetic field on to the integrated CMOS magnetoresistive biochips 132 under test.

There can be two directions for the magnetic field applied by electromagnet 41, either parallel or perpendicular to the surface of integrated CMOS magnetoresistive biochip 132. With proper signal processing scheme, field in either direction can magnetize the magnetic particles to stimulate magnetoresistive sensor biochip and test the existence of magnetic particles. In the present invention, the field direction is perpendicular to the surface of the integrated CMOS magnetoresistive biochip. Device 43 is used to tune the direction of electromagnet 41 to ensure that the magnetic field is perpendicular to magnetoresistive sensor biochip 132.

According to the response of magnetoresistive sensor biochips 132 to the magnetic field applied by electromagnet 41, microprocessor 6 can calculate the direction of magnetic field, and then instructs device 43 to adjust electromagnet 41 accordingly.

Electronic module 5, which is used for controlling and reading information from the biochip 132, is connected to biochip 132 via conductive lines 191 on substrate 111 on cartridge 1. The function of electronic module 5 is supply power and control signals for magnetoresistive sensor biochip 132 in said cartridge 1, test the information stored in each magnetoresistive sensor elements in biochip 132, and perform analog-to-digital conversion of the results.

Microprocessor 6 controls and coordinates the operation of the means for applying pressure 2, fluid injection system 3, means for generating a magnetic field 4 and electronic module 5. Additionally, microprocessor 6 is also used to processes information and test results, such as performing the necessary calculation to remove background noise and extract out the user data.

User interface 7 is connected to microprocessor 6 to receive users' instruction and display the test condition and results.

Embodiment 7

Figure 7:
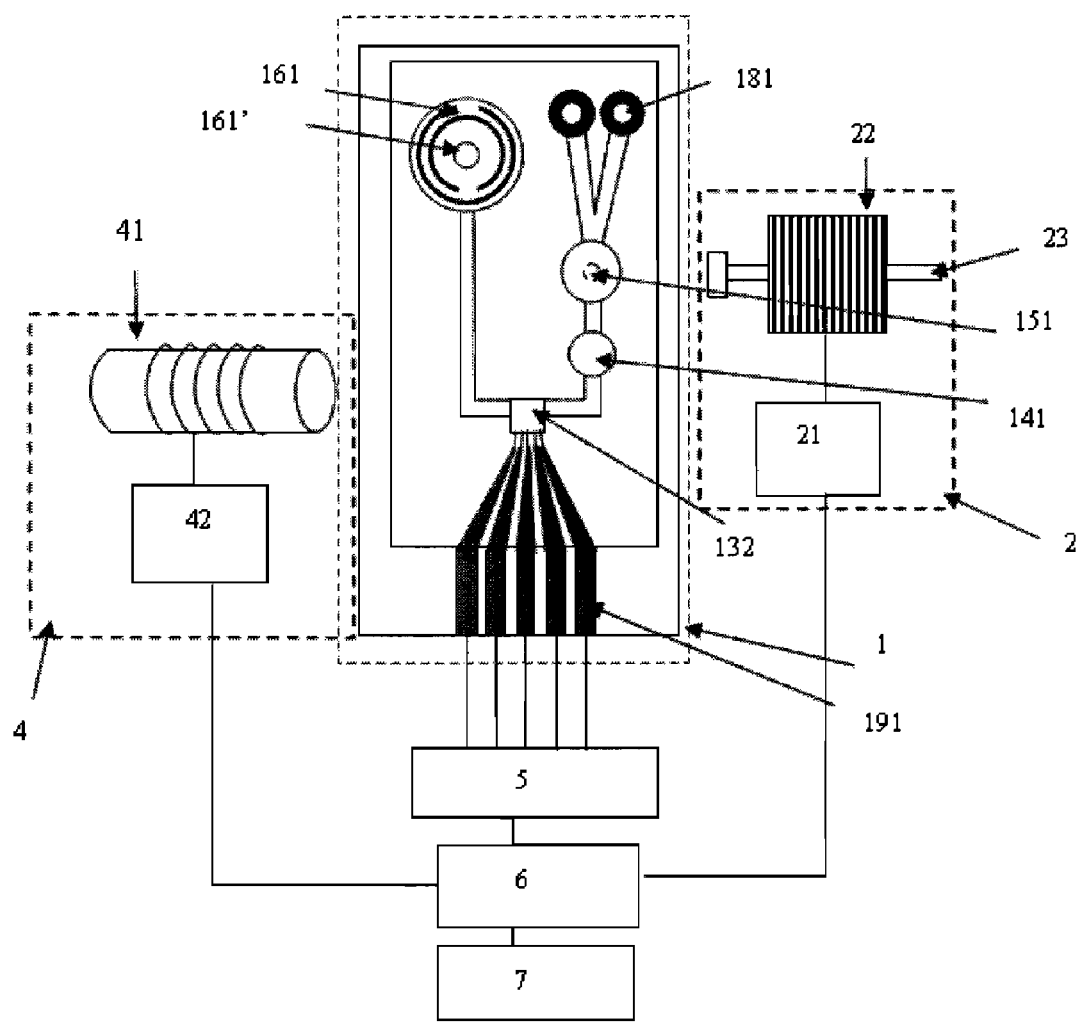
FIG. 7 shows the testing apparatus for magnetoresistive sensor biochips in the seventh embodiment.

Shown in FIG. 7 is a testing apparatus for magnetoresistive sensor biochips including means for applying pressure 2, which comprises an electronic motor or electronic stepping motor 22, and the control circuit of the electronic stepping motor 21, the output of which are controlled by microprocessor 6. In application, solution inlet 181 is sealed first, and then driving rod 23, which is the actuation structure of said electrical motor or electrical stepping motor, put pressure on pump chamber 151 to inject liquid in reagent reservoir 141 into or through reaction chamber 131 in said cartridge 1.

The testing apparatus shown in FIG. 7 further includes 4, the means for generating a magnetic field, which comprises electromagnet 41 in series connection with power circuit 42. The operation of power circuit 42 is controlled by microprocessor 6. Power circuit 42 provides either a positive or negative current with particular amplitude to the electromagnet. Accordingly, the electromagnet applies either a positive or negative magnetic field on to the integrated CMOS magnetoresistive biochip 132 in reaction chamber 131.

There can be two directions for the magnetic field applied by electromagnet 41, either parallel or perpendicular to the surface of integrated CMOS magnetoresistive biochip 132 in reaction chamber 131. With proper signal processing scheme, field in either direction can magnetize the magnetic particles to stimulate magnetoresistive sensor biochip and test the existence of magnetic particles. In the present invention, the field direction is perpendicular to the surface of the integrated CMOS magnetoresistive biochip. Device 43 is used to tune the direction of electromagnet 41 to ensure that the magnetic field is perpendicular to magnetoresistive sensor biochip 132 in reaction chamber 131.

According to the response of magnetoresistive sensor biochips 132 to the magnetic field applied by electromagnet 41, microprocessor 6 can calculate the direction of magnetic field, and then instructs device 43 to adjust electromagnet 41 accordingly.

Electronic module 5, which is used for controlling and reading information from the biochip 132 in reaction chamber 131, is connected with biochip 132 via conductive lines 191 on substrate 111 on cartridge 1. The function of electronic module 5 is supply power and control signals for magnetoresistive sensor biochips 132, test the information stored in each magnetoresistive sensor elements in biochip 132, and perform analog-to-digital conversion of the results;

Microprocessor 6 controls and coordinates the operation of the means for applying pressure 2, means for generating a magnetic field 4 and electronic module 5. Additionally, microprocessor 6 is also used to processes information and test results, such as performing the necessary calculation to remove background noise and extract out the user data.

User interface 7 is connected to microprocessor 6 to receive users' instruction and display the test condition and results.

In comparison with embodiments 2, 4, and 6, this embodiment is not equipped with a microfluidic injection system. As a result, the many types of fluid can be injected by off-line peristaltic pumps or syringes. Fluid inlets 181 are sealed after sample addition, and then pressure is applied on pump chamber 151 by the test apparatus to start testing.

Embodiment 8

Figure 8:
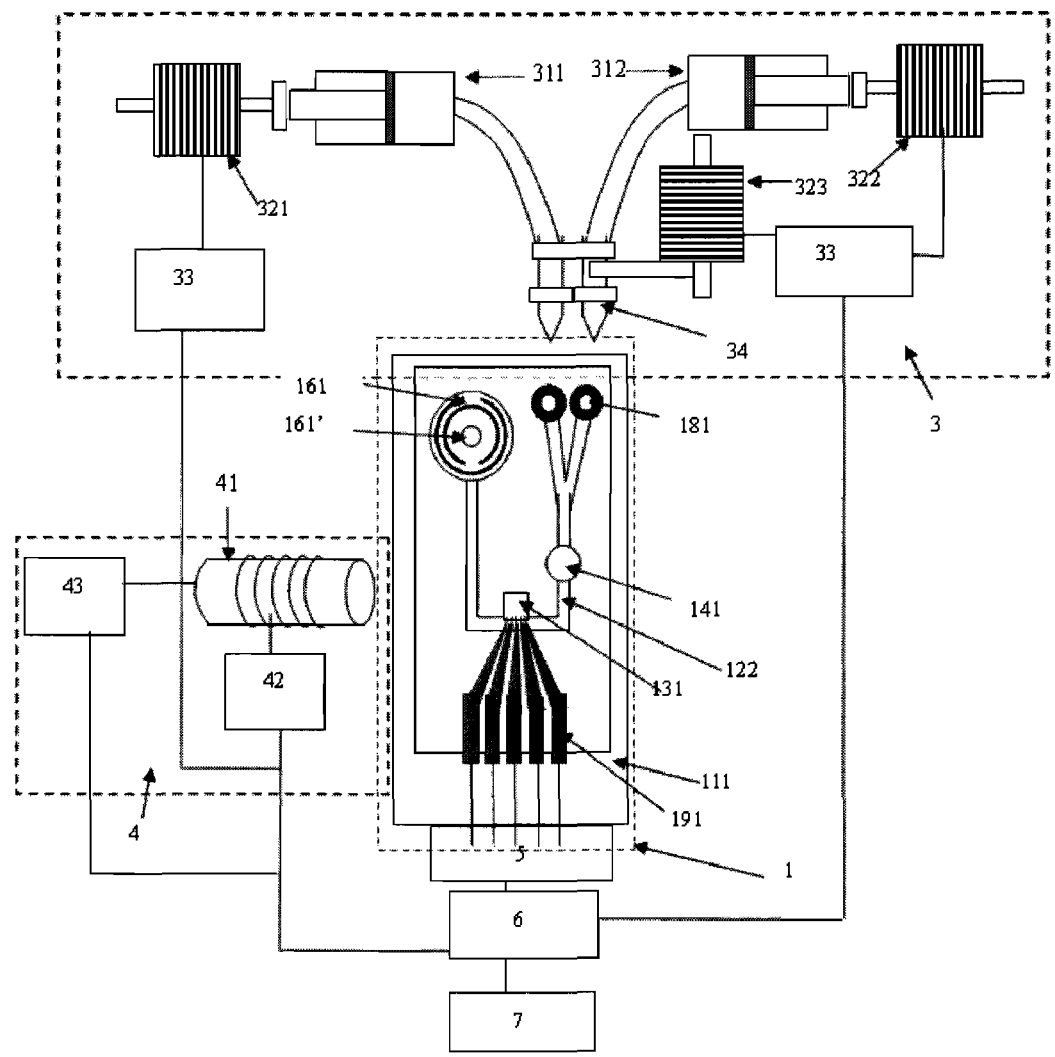
FIG. 8 shows the testing apparatus for magnetoresistive sensor biochips in the eighth embodiment.

Refer to FIG. 8 for this embodiment. The testing apparatus for integrated CMOS magnetoresistive biochips includes: fluid injection system 3 which comprises: the first injector 311 and the second injector 312; the first stepping electrical motor 321, the second stepping electrical motor 322, the third stepping electrical motor 323; the control circuits for the stepping motors 33; injection needle 34. The driving rod of the first electrical stepping motor 321 actuates the first injector 311; the driving rod of the second electrical stepping motor 322 actuates the second injector 312. Injection needles 34, which are connected with liquid injectors 311 and 312, are driven by the third electrical stepping motor 323 to form fluid-tight connection with fluid inlet 181 in cartridge 1. The output of control circuits 33 is regulated by microprocessor 6. Driven by electrical stepping motors 321 and 322, the first injector 311 and second injector 312 inject fluid, either successively or simultaneously, into reaction chamber 131 via an inlet or inlets 181 connected to reaction chamber 131 through microfluidic channels 122. Said liquid stream can also drive the fluid in microfluidic channels 122 into the waste reservoir 161 through the reaction chamber 131 to drain the waste through liquid outlet 161'. The liquid stream ejected by fluid injection system 3 contains biomolecules, magnetic particles or buffer solution.

The testing apparatus shown in FIG. 8 further includes 4, the means for generating a magnetic field, which comprises electromagnet 41 in series connection with power circuit 42. The operation of power circuit 42 is controlled by microprocessor 6. Power circuit 42 provides either a positive or negative current with a particular amplitude to the electromagnet. Accordingly, the electromagnet applies either a positive or negative magnetic field on to the integrated CMOS magnetoresistive biochips 132 in reaction chamber 131.

There can be two directions for the magnetic field applied by electromagnet 41, either parallel or perpendicular to the surface of integrated CMOS magnetoresistive biochip 132 in reaction chamber 131. With proper signal processing scheme, field in either direction can magnetize the magnetic particles to stimulate magnetoresistive sensor biochip and test the existence of magnetic particles. In the present invention, the field direction is perpendicular to the surface of the integrated CMOS magnetoresistive biochip. Device 43 is used to tune the direction of electromagnet 41 to ensure that the magnetic field is perpendicular to magnetoresistive sensor biochip 132.

According to the response of magnetoresistive sensor biochips 132 to the magnetic field applied by electromagnet 41, microprocessor 6 can calculate the direction of magnetic field, and then instructs device 43 to adjust electromagnet 41 accordingly.

Electronic module 5, which is used for controlling and reading information from the biochip 132, is connected with biochip 132 via conductive lines 191 on substrate 111 on cartridge 1. The function of electronic module 5 is supply power and control signals for magnetoresistive sensor biochips 132 in said cartridge 1, test the information stored in each magnetoresistive sensor elements in biochip 132, and perform analog-to-digital conversion of the results;

Microprocessor 6 controls and coordinates the operation of fluid injection system 3, means for generating a magnetic field 4 and electronic module 5. Additionally, microprocessor 6 is also used to processes information and test results, such as performing the necessary calculation to remove background noise and extract out the user data.

User interface 7 is connected to said microprocessor 6 to receive users' instruction and display the test condition and results.

In comparison with embodiment 2, embodiment 8 does not have means for applying pressure to a pumping chamber on the cartridge; all fluid in microfluidic channels is driven by fluid injector 3.

Embodiment 9

Figure 9:
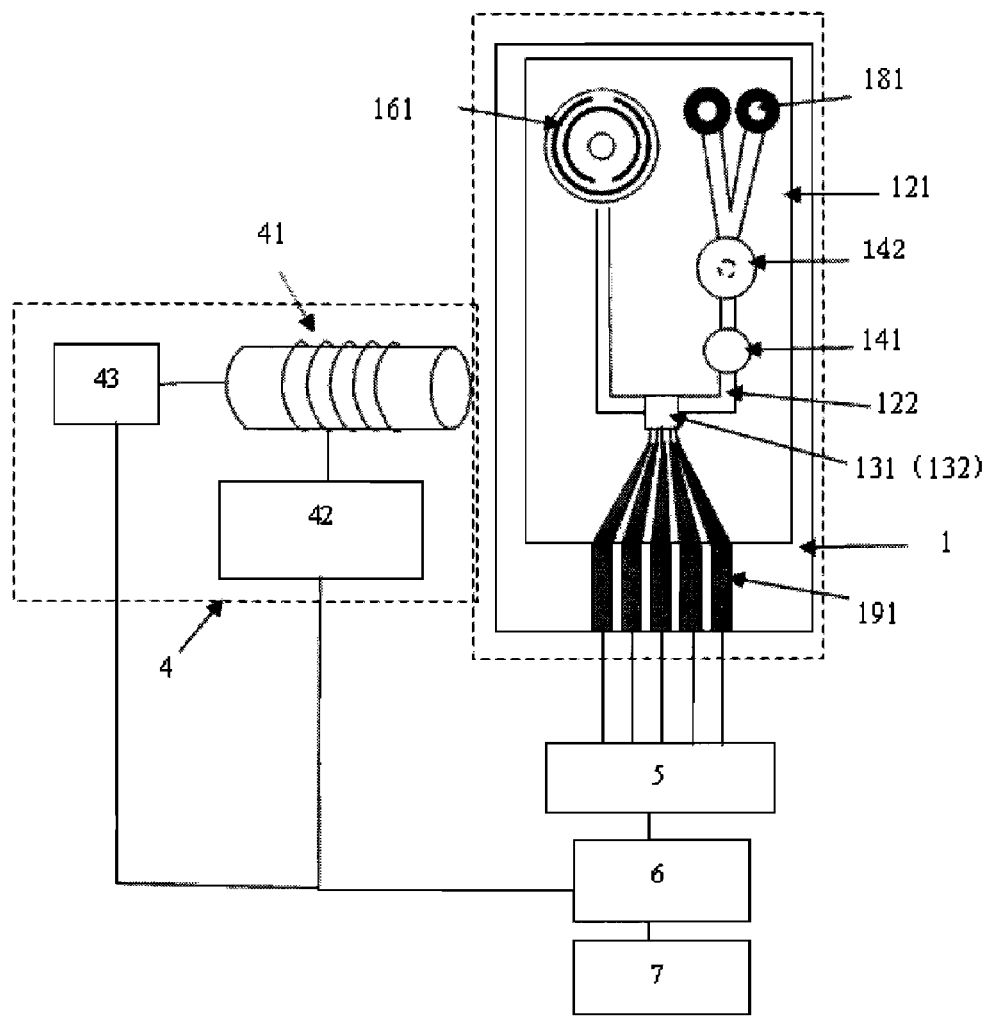
FIG. 9 shows the testing apparatus for magnetoresistive sensor biochips in the ninth embodiment.

A Testing Apparatus for Magnetoresistive Sensor Biochips is shown in FIG. 9, which mainly includes:

means for generating a magnetic field 4 comprising electromagnet 41 and power circuit 42 for the electromagnet. Either a positive or negative current with required amplitude can be provided to the electromagnet, which accordingly applies either a positive or negative magnetic field to biochip 132 in cartridge 1. Biochip 132 is placed in reaction chamber 131.

Electronic module 5, which is used for controlling and reading information from the biochip 132, is connected with biochip 132 via conductive lines 191 on substrate 111 on cartridge 1. The function of electronic module 5 is to supply power and control signals for magnetoresistive sensor biochips 132 in said cartridge 1, test the information stored in each magnetoresistive sensor elements in biochip 132, and perform analog-to-digital conversion of the results;

Microprocessor 6 controls and coordinates the operation of means for applying magnetic field 4 and electronic module 5. Additionally, microprocessor 6 is also used to processes information and test results, such as performing the necessary calculation to remove background noise and extract out the user data.

User interface 7 is connected to microprocessor 6 to receive users' instruction and display the test condition and results.

The structure of the cartridge used in this embodiment is detailed in the description of embodiment 1. Embodiment 9 is characterized by a simplified architecture for not having fluid injection system 3 and means for applying pressure 2, which may be on a separate system dedicated to facilitate the biochemical reaction and hybridization process.

The aforementioned embodiments show the details of the many aspects of the present invention. However, many modifications and variations of the embodiments can be made without departing from the spirit and scope of the present invention, as will be apparent to those skilled in the art. The specific embodiments described herein are offered by way of example only, and the invention is to be limited only by the terms of the appended claims, along with the full scope of equivalents to which such claims are entitled.

The invention claimed is:

1. An apparatus for automatically testing integrated CMOS magnetoresistive biochip comprising:
    means for applying pressure directly or indirectly to a cartridge;
    a liquid injection system connected to the cartridge for injecting liquid into the microfluidic channel or channels in said cartridge,
    means for generating a magnetic field, by providing, according to requirements, a positive or negative current with certain intensity to a electromagnet to generate a positive or negative magnetic field with certain intensity, and for applying the positive or negative magnetic field to said integrated CMOS magnetoresistive biochip on said cartridge;
    an electronic module for controlling and reading information from said biochip, to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal;
    a microprocessor to control and coordinate the operation of the following components: said means for applying pressure, said liquid injection system, said means for generating a magnetic field, and said electronic module for controlling and reading information from the biochip, and to process information measured under different magnetic fields;
    a user interface connected to the microprocessor to receive and display information from said microprocessor.

2. The apparatus in claim 1, wherein the means for applying pressure comprises an electrical motor or electrical stepping motor, and means for generating a vacuum or pressure;
    said electrical motor or electrical stepping motor is used for applying pressure directly to a reagent reservoir in said cartridge or applying pressure to a pump chamber connected to said reagent reservoir to pump the fluid in said reagent reservoir into said reaction chamber in said cartridge;
    said means for generating a vacuum or pressure is used for applying pressure to a pump chamber or waste reservoir connected to the reagent reservoir in the cartridge to pump the fluid into said reaction chamber in said cartridge.

3. The apparatus in claim 1, wherein said liquid injection system comprises:
    an injector or a plurality of injectors to inject fluid into said microfluidic channel or channels via a fluid inlet or inlets connected to the microfluidic channel or channels in the cartridge;
    an injection needle or needles connected to said fluid inlet or inlets in the cartridge.

4. The apparatus in claim 1, wherein the liquid injected by said injector or plurality of injectors of said fluid injection system contains biomolecules, magnetic particles or buffer solution.

5. The apparatus in claim 1, wherein the direction of said magnetic field is changed automatically according to the instruction of said microprocessor.

6. The apparatus in claim 1, wherein said integrated CMOS magnetoresistive biochip is an electro-magnetic device comprising the large scale integrated CMOS circuit integrated with magnetoresistive device manufactured with semiconductor processing technology, including CMOS circuit integrated with magnetic tunnel junction arrays, or CMOS circuit integrated with giant magneto-resistive devices, or CMOS circuit integrated with Hall effect magneto-resistance devices.

7. An apparatus for automatically testing integrated CMOS magnetoresistive biochip comprising:
   means for applying pressure directly or indirectly to a cartridge;
   means for generating a magnetic field, by providing, according to requirements, a positive or negative current with certain intensity to a electromagnet to generate a positive or negative magnetic field with certain intensity, and for applying the positive or negative magnetic field to said integrated CMOS magnetoresistive biochip on said cartridge;
   an electronic module for controlling and reading information from said biochip to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal;
   a microprocessor to control and coordinate the operation of the following components: said means for applying pressure, said liquid injection system, said means for generating a magnetic field, and said electronic module for controlling and reading information from the biochip, and to process information measured under different magnetic fields;
   a user interface connected to the microprocessor to receive and display information from said microprocessor.

8. The apparatus in claim 7, wherein the means for applying pressure comprises an electrical motor or electrical stepping motor, and means for generating a vacuum or pressure;
   said electrical motor or electrical stepping motor is used for applying pressure directly to a reagent reservoir in said cartridge or applying pressure to a pump chamber connected to said reagent reservoir to pump the fluid in said reagent reservoir into said reaction chamber in said cartridge;
   said means for generating a vacuum or pressure is used for applying pressure to a pump chamber or waste reservoir connected to the reagent reservoir in the cartridge to pump the fluid into said reaction chamber in said cartridge.

9. The apparatus in claim 7, wherein the direction of said magnetic field is changed automatically according to the instruction of said microprocessor.

10. The apparatus in claim 7, wherein said integrated CMOS magnetoresistive biochip is an electro-magnetic device comprising the large scale integrated CMOS circuit integrated with magnetoresistive device manufactured with semiconductor processing technology, including CMOS circuit integrated with magnetic tunnel junction arrays, or CMOS circuit integrated with giant magneto-resistive devices, or CMOS circuit integrated with Hall effect magneto-resistance devices.

11. An apparatus for automatically testing integrated CMOS magnetoresistive biochips comprising:
   a liquid injection system connected to the cartridge for injecting liquid into the microfluidic channel or channels in said cartridge,
   means for generating a magnetic field, by providing, according to requirements, a positive or negative current with certain intensity to a electromagnet to generate a positive or negative magnetic field with certain intensity, and for applying the positive or negative magnetic field to said integrated CMOS magnetoresistive biochip on said cartridge;
   an electronic module for controlling and reading information from said biochip, to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal;
   a microprocessor to control and coordinate the operation of the following components: said means for applying pressure, said liquid injection system, said means for generating a magnetic field, and said electronic module for controlling and reading information from the biochip, and to process information measured under different magnetic fields;
   a user interface connected to the microprocessor to receive and display information from said microprocessor.

12. The apparatus in claim 11, wherein the liquid injection system contains:
   an injector or a plurality of injectors for injecting liquid into said microfluidic channel or channels via a fluid inlet or inlets connected to the microfluidic channel or channels in the cartridge;
   an injection needle or needles connected to said fluid inlet or inlets in the cartridge.

13. The apparatus in claim 11, wherein the liquid injected by said injector or plurality of injectors of said fluid injection system contains bio-molecules, magnetic particles or buffer solution.

14. The apparatus in claim 11, wherein the direction of said magnetic field is changed automatically according to the instruction of said microprocessor.

15. The apparatus in claim 11, wherein said integrated CMOS magnetoresistive biochip is an electro-magnetic device comprising the large scale integrated CMOS circuit integrated with magnetoresistive device manufactured with semiconductor processing technology, including CMOS circuit integrated with magnetic tunnel junction arrays, or CMOS circuit integrated with giant magneto-resistive devices, or CMOS circuit integrated with Hall effect magneto-resistance devices.

16. An apparatus for automatically testing integrated CMOS magnetoresistive biochip comprising:
   means for generating a magnetic field, by providing, according to requirements, a positive or negative current with certain intensity to a electromagnet to generate a positive or negative magnetic field with certain intensity, and for applying the positive or negative magnetic field to said integrated CMOS magnetoresistive biochip on said cartridge;
   an electronic module for controlling and reading information from said biochip, to supply power and control signal to said integrated CMOS magnetoresistive biochip in said cartridge, communicate with a large scale integrated CMOS circuit on the biochip, test the information stored in the sensing elements of the integrated CMOS magnetoresistive biochip, and convert the tested analog signal to digital signal;
   a microprocessor to control and coordinate the operation of the following components: said means for applying pressure, said liquid injection system, said means for generating a magnetic field, and said electronic module for controlling and reading information from the biochip, and to process information measured under different magnetic fields;

a user interface connected to the microprocessor to receive and display information from said microprocessor.

17. The apparatus in claim 16, wherein the direction of the magnetic field is changed automatically according to the instruction of said microprocessor.

18. The apparatus in claim 16, wherein said integrated CMOS magnetoresistive biochip is an electro-magnetic device comprising a large scale CMOS circuit integrated with magnetoresistive device manufactured with semiconductor processing technology, including CMOS circuit integrated with magnetic tunnel junction arrays, or CMOS circuit integrated with giant magneto-resistive devices, or CMOS circuit integrated with Hall effect magneto-resistance devices.

* * * * *